US008652112B2

(12) United States Patent  
Johannison et al.

(10) Patent No.: US 8,652,112 B2
(45) Date of Patent: Feb. 18, 2014

(54) OSTOMY DEVICE

(75) Inventors: Ulf Johannison, Landvetter (SE); Päranders Wärja, Hindås (SE)

(73) Assignee: Molnlycke Health Care AB, Gothenburg (SE)

( * ) Notice: Subject to any disclaimer, the term of this patent is extended or adjusted under 35 U.S.C. 154(b) by 0 days.

(21) Appl. No.: 13/581,705

(22) PCT Filed: Feb. 4, 2011

(86) PCT No.: PCT/SE2011/050131
§ 371 (c)(1),
(2), (4) Date: Aug. 29, 2012

(87) PCT Pub. No.: WO2011/108972
PCT Pub. Date: Sep. 9, 2011

(65) Prior Publication Data
US 2012/0323193 A1 Dec. 20, 2012

Related U.S. Application Data

(60) Provisional application No. 61/314,616, filed on Mar. 17, 2010.

(30) Foreign Application Priority Data

Mar. 2, 2010 (SE) ........................ 1050193

(51) Int. Cl.
*A61F 5/448* (2006.01)
*A61F 5/447* (2006.01)
*A61F 5/445* (2006.01)

(52) U.S. Cl.
USPC ........... 604/344; 604/327; 604/332; 604/336; 604/338; 604/339; 604/340; 604/342; 604/343

(58) Field of Classification Search
USPC ......... 604/344, 327, 332, 336, 337, 338, 339, 604/340, 341, 342, 343
See application file for complete search history.

(56) References Cited

U.S. PATENT DOCUMENTS 4,419,100 A * 12/1983 Alexander .................. 604/339
4,642,107 A * 2/1987 Arnone et al. .............. 604/342

(Continued)

FOREIGN PATENT DOCUMENTS

| EP | 1557145 | 7/2005 |
| GB | 1274382 | 5/1972 |
| WO | WO 2006/075950 | 7/2006 |

OTHER PUBLICATIONS

International Search Report issued on May 20, 2011 for International Application No. PCT/SE2011/050131 (WO 2011/108972), which was filed on Feb. 4, 2011 [Inventor — Johannison; Applicant— Mölnlycke Health Care AB] [4 pages].

(Continued)

*Primary Examiner* — Adam Marcetich
(74) *Attorney, Agent, or Firm* — Ballard Spahr LLP

(57) ABSTRACT

An ostomy device is provided including an ostomy pouch having an entrance opening, a body attachment wafer having a through-going opening and a coupling layer, which couples the pouch to the body attachment wafer and has a central opening therein. The body attachment wafer includes a plastic film, which is coated with a layer of skin friendly adhesive on the side thereof distal to the ostomy pouch. The coupling layer is affixed to the body attachment wafer along an attachment line extending around the central opening in the coupling layer, the attachment line being distanced from the central opening in the coupling layer. The region around the entrance opening of the pouch is affixed to the coupling layer in a landing zone located between the attachment line and the opening in the body attachment wafer.

14 Claims, 1 Drawing Sheet

(56) References Cited

U.S. PATENT DOCUMENTS

| | | | |
|---|---|---|---|
| 4,648,875 A * | 3/1987 | Ferguson | 604/339 |
| 4,973,323 A | 11/1990 | Kaczmarek | 604/339 |
| 5,167,651 A * | 12/1992 | Leise et al. | 604/339 |
| 5,330,454 A * | 7/1994 | Klingler et al. | 604/338 |
| 5,730,735 A * | 3/1998 | Holmberg et al. | 604/338 |
| 5,997,989 A * | 12/1999 | Gessner et al. | 428/152 |
| 6,106,507 A * | 8/2000 | Botten et al. | 604/338 |
| 2002/0082570 A1* | 6/2002 | Mishima et al. | 604/332 |
| 2003/0204173 A1 | 10/2003 | Burns, Jr. | 604/385.19 |
| 2004/0059306 A1 | 3/2004 | Tsal | 604/317 |
| 2007/0027434 A1* | 2/2007 | Pedersen et al. | 604/333 |
| 2007/0219514 A1* | 9/2007 | Strobech | 604/336 |
| 2008/0114278 A1* | 5/2008 | Fabo et al. | 602/48 |
| 2010/0137821 A1* | 6/2010 | Hansen et al. | 604/338 |
| 2010/0241093 A1* | 9/2010 | Hooper | 604/339 |
| 2011/0071485 A1* | 3/2011 | Foley et al. | 604/342 |

OTHER PUBLICATIONS

Written Opinion issued on May 20, 2011 for International Application No. PCT/SE2011/050131 (WO 2011/108972), which was filed on Feb. 4, 2011 [Inventor—Johannison; Applicant—Molnlycke Health Care AB] [4 pages].

International Preliminary Report on Patentability issued on Sep. 4, 2012 for International Application No. PCT/SE2011/050131 (WO 2011/108972), which was filed on Feb. 4, 2011 [Inventor—Johannison; Applicant—Molnlycke Health Care AB] [5 pages].

* cited by examiner

OSTOMY DEVICE

CROSS-REFERENCE TO RELATED APPLICATIONS

The present application is a U.S. National Phase Application of International Application No. PCT/SE2011/050131, filed Feb. 4, 2011, which claims priority to Swedish Patent Application No. 1050193-0, filed Mar. 2, 2010, and U.S. Patent Application No. 61/314,616, filed Mar. 17, 2010, all of which applications are incorporated herein fully by this reference.

TECHNICAL FIELD

The present invention relates to an ostomy device including an ostomy pouch having an entrance opening, a body attachment wafer having a through-going opening and a coupling layer, which couples the pouch to the body attachment wafer and consists of a plastic film, said body attachment wafer includes a plastic film, which is coated with a skin friendly adhesive on the side thereof distal to the ostomy pouch.

BACKGROUND OF THE INVENTION

It is essential that an ostomy device is attached to the body of the wearer in a secure way. Furthermore, such a device must be attached to the body of the wearer so that liquid or odour will not leak out to the environment surrounding the ostomy device. The skin around a stoma opening in the body is usually very sensitive so liquid from the stoma opening leaking onto the skin of the wearer has a detrimental effect on the skin. It is therefore important to prevent liquid from the stoma opening from leaking, not only out to the environment but also onto the skin surrounding the stoma opening.

EP 1 557 145 discloses an ostomy device of the kind described above in which a coupling layer reduces the degree of coupling between the ostomy pouch and the body attaching wafer in order to reduce the risk for detachment of a body attachment wafer attached to a wearer. The body attachment wafer known from EP 1 557 145 consists of one or more plastic layers and an adhesive layer comprising one or more hydrocolloid polymers. Also GB 1 274 382 discloses an ostomy device having a similar coupling layer.

SUMMARY OF THE INVENTION

The objective of the present invention is to provide an ostomy device in which the permeability and the softness of the body attachment wafer is not influenced to a high degree by the coupling of the ostomy pouch to the body attachment wafer and in which the risk for detachment of the body attachment wafer due to forces caused by the weight of the pouch and its content is reduced to a large extent.

This objective is accomplished by an ostomy device including an ostomy pouch having an entrance opening, a body attachment wafer having a through-going opening and a coupling layer, which couples the pouch to the body attachment wafer and has a central opening therein, said body attachment wafer includes a plastic film which is coated with a layer of skin friendly adhesive on the side thereof distal to the ostomy pouch, characterized in that the coupling layer is affixed to the body attachment wafer along an attachment line extending around the central opening in the coupling layer, said attachment line being distanced from the central opening in the coupling layer, and the region around the entrance opening of the pouch is affixed to the coupling layer in a landing zone located between said attachment line and the opening in the body attachment wafer. By having a thin coupling layer affixed to the body attachment wafer, the permeability and softness of the wafer will not be reduced to a high degree in the affixing region and by affixing the coupling layer to the wafer in the outer periphery thereof the forces caused by the weight of the pouch and its content is transferred to the body attachment wafer distal from the outer and inner peripheries thereof, thereby minimizing peeling forces on the outer and inner edges of the body attachment wafer. Furthermore, the risk for wrinkles appearing in the body attachment wafer due to forces transferred from the ostomy pouch is reduced to a large extent.

In a preferred embodiment, the plastic film in the body attachment wafer has a thickness of 50 micrometer at the most and the grammage of the coupling layer is 15-60 $g/m^2$. The coupling layer can consist of a plastic film, preferably a polyurethane film, non-permeable plastic foam or a laminate of a plastic film and a nonwoven.

In a second preferred embodiment, the inner periphery of the coupling layer is affixed to the body attachment wafer. Thereby, liquid from the stoma opening can not gather between the coupling layer and the body attachment wafer. In order to ventilate the region between the coupling layer and the wafer, the attachment line can be constituted by a discontinuous seam or the coupling layer may comprise perforations in an area thereof between the landing zone and the attachment line.

Moreover, the inner periphery of the coupling layer being distanced from the outer periphery of the through going opening in the body attachment wafer, whereby the opening in the body attachment wafer can be adapted to the size and shape of a stoma of a patient by cutting without risk for damaging the coupling layer.

The attachment line of the coupling layer is preferably distanced from the outer periphery of the body attachment wafer by at least 5 mm.

The skin friendly adhesive is preferably a silicone gel, which has a weight per unit area greater than 50 $g/m^2$ and a penetration value greater than 10 mm.

BRIEF DESCRIPTION OF THE DRAWINGS

The invention will now be described with reference to the enclosed figures, of which.

DESCRIPTION OF EMBODIMENTS

Figure 1:
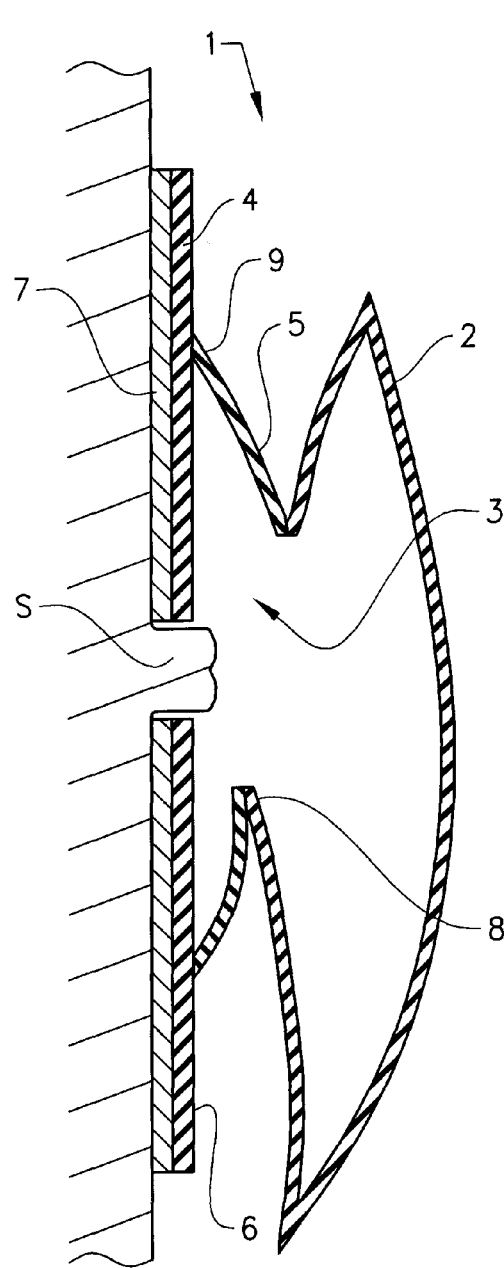
FIG. 1 schematically shows a cross sectional view of an ostomy device according to a first embodiment of the invention, and FIG. 2 schematically shows a similar view of a second embodiment of the invention.

The ostomy device 1 in the embodiment schematically shown in FIG. 1 comprises an ostomy pouch 2 having an entrance opening 3, a body attachment wafer 4 and a coupling layer 5 for coupling the ostomy pouch 2 to the body attachment wafer 4. The coupling layer 5 has an opening having a size corresponding to the opening 3 of the ostomy pouch and is affixed to the ostomy pouch in a region surrounding said openings. The coupling layer 5 is furthermore affixed to the body attachment wafer 4 along an attachment line 9 at its outer periphery. The ostomy device 1 is in FIG. 1 schematically shown attached to the skin of a wearer around the stoma S.

The body attachment wafer 4 consists of a plastic film 6 which is coated with a layer 7 of soft and tacky silicone gel.

Such an adhesive is skin friendly and has an excellent sealing effect. Examples of silicone gel adhesives suitable to be used as coating on the plastic film 6 are given in WO2006/075950, which is referred to in this respect. Such silicone gel adhesives should have a softness measured as a penetration value of 20-10 mm and a weight per unit area of at least 50 g/m$^2$, whereby the weight per unit area increases with decreasing softness. The softness is measured by a method based on ASTM D 937 and described in WO2006/075950, which is referred to in this respect.

The plastic film 6 of the body attachment wafer should be thin in order to ensure that the stiffness of the film will not prevent the silicone gel adhesive from penetrating into all irregularities in the skin. The plastic film 6 should therefore have a thickness that does not exceed 50 micrometers.

If affixing the ostomy pouch 2 directly to the body attachment wafer, the combined materials in this region, i.e. the material around the opening 3 of the ostomy pouch and the plastic film 6 and the silicone gel adhesive layer 7 of the body attachment wafer 4, would give rise to higher stiffness than in the rest of body attachment wafer. Such an increased stiffness would make it more difficult for the body attachment wafer to follow the irregularities of the skin in this fastening region and would thus increase the risk for local and involuntary detachment of the body attachment wafer in this fastening region during use. Such a local detachment of the body attachment wafer can eventually lead to local leakage or total detachment of the body attachment wafer. Furthermore, since the material in ostomy pouch 2 is not permeable, the skin can not be ventilated in this fastening region which could cause moisture to gather on the skin in this fastening region, which in turn can lead to local detachment of the body attachment wafer and eventually to total detachment thereof. The fastening region would also be located relatively close to a stoma which means that local detachment can cause local leakage of liquid from the ostomy pouch to leak onto the skin.

By providing a coupling layer 5 between the body attachment wafer 4 and the ostomy pouch 2 it can be ensured that in the fastening region, in which the coupling layer 5 is affixed to the body attachment wafer 4, the vapour permeability would not be negatively affected while still providing less stiffness. The coupling layer is preferably welded to the plastic film 6 of the body attachment wafer 4 along its outer periphery. The grammage, i.e. weight per unit area, of the coupling layer 5 is 15-60 g/m$^2$, preferably 20-40 g/m$^2$. By the use of such a thin coupling layer 5 the combined stiffness of the two layers 5,6 welded together in the fastening region is considerably lower than the stiffness of the ostomy pouch 2 in the region thereof surrounding the entrance opening 3 and the decrease in vapour permeability in the fastening region due to the presence of the coupling layer 5 is not significant.

By having the ostomy pouch 2 affixed to the coupling layer in a landing zone 8 around the opening 3, the distribution of forces acting on the body attachment wafer 4 due to the weight of the ostomy pouch 2 and its content and to external forces acting on the ostomy pouch 2 is favourably influenced. The attachment line 9 affixing the coupling layer to body attachment wafer is distanced from both the outer and inner periphery of the body attachment wafer 4 so the forces from the ostomy pouch 2 is transferred via the coupling layer 5 to the body attachment wafer 4 at a distance from both the outer and inner edge thereof. Thereby the forces from the ostomy pouch 2 will be transferred to the body attachment wafer mainly as shear forces and the risk for peel forces to act on the inner and outer edge of the body attachment wafer is minimized.

The ostomy pouch 2 is affixed to the coupling layer 5 in a landing zone 8 which in the embodiment according to FIG. 1 is a region surrounding the opening of the coupling layer 5. The ostomy pouch 2 is reinforced by an annular layer of plastic material in a region surrounding its opening 3 and this layer is adhesively attached to the landing zone of the coupling layer 5. The ostomy pouch 2 comprises an inner layer of plastic material and preferably an outer layer of soft nonwoven.

The plastic film 6 in the body attachment wafer 4 consists preferably of polyurethane (PU) but other plastic material such as polyethylene (PE) and ethylene-vinyl acetate (EVA) can also be used.

The coupling layer 5 consists preferably of a film of polyurethane (PU) but other plastic materials can also be used. A thin non-permeable foam or a laminate of plastic film and nonwoven is also possible to use.

The plastic material in the ostomy pouch 2 should be liquid impermeable as well as vapour impermeable.

Figure 2:
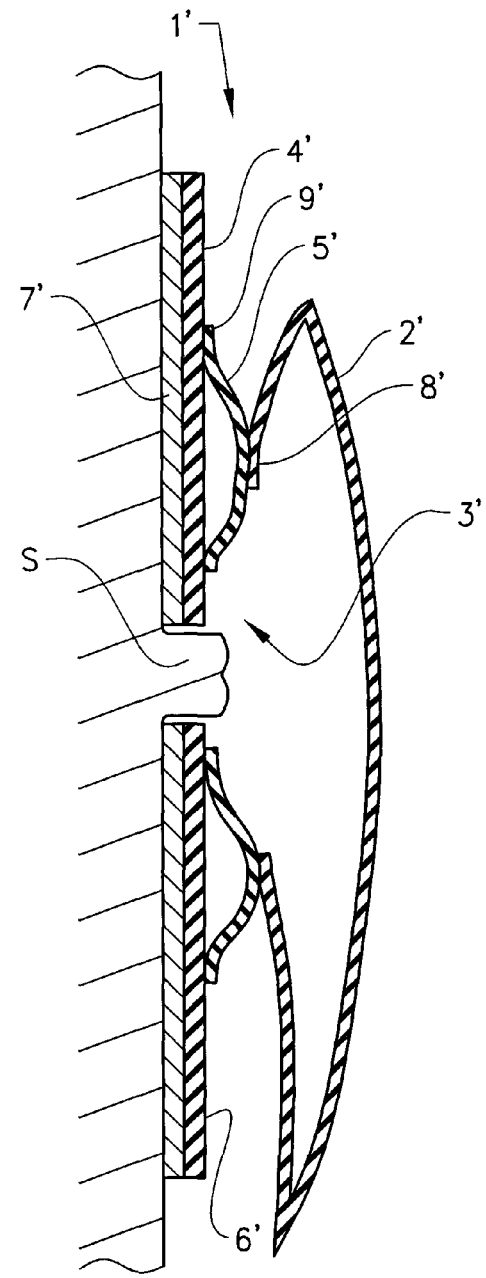

In FIG. 2, a second embodiment of an ostomy device 1' in accordance with the present invention is schematically shown in a cross sectional view. The ostomy device 1' differs from the ostomy device 1 shown in FIG. 1 mainly in that the coupling layer 5' is affixed to the body attachment wafer 4' along both the outer an inner peripheries of the coupling layer 5' and that the landing zone 8' for the ostomy pouch 2' is located at a distance from both the outer and inner edges of the coupling layer 5' instead of along the inner edge as is the case in the first embodiment according to FIG. 1. Components in the second embodiment described with reference to FIG. 2 are given the same reference number as similar components in the embodiment of FIG. 1 with the addition of a prime sign.

In order not to impair the ventilation ability of the body attachment wafer 4' in the space between the coupling layer 5' and the body attachment wafer 4', this space is ventilated for example by having the outer peripheral region of the coupling layer affixed to the body attachment wafer by a discontinuous weld seam. In a variant holes are made in the coupling layer 5' in the area between the landing zone 8', in which the ostomy pouch 2' is affixed to the coupling layer 5', and the outer periphery of the of the coupling layer 5'. It is of course possible to both have holes in said area and a discontinuous weld seam along the outer periphery of the coupling layer. The inner peripheral region of the coupling layer 5' is affixed to the body attachment wafer 4' by a continuous weld seam to prevent leakage.

The ostomy pouch is so disposed on a body of a patient that liquid waste from stoma S will flow downwardly after leaving the stoma. By having the inner edge of the coupling layer 5' affixed to the body attachment wafer 4', it is ensured that the first liquid waste leaving the stoma will flow to the lower part of the ostomy pouch 2', i.e. downwards in FIG. 2, and not gather near the stoma as might happen in the case of the first embodiment according to FIG. 1, in which there is a risk that liquid waste can leak into the lower part of the space between the coupling layer 5 and the body attachment wafer 4. In this respect it is pointed out that this space is greatly exaggerated in the figures. When manufacturing the ostomy devices according to FIGS. 1 and 2, coupling layers 5,5' are planar annular layers laid onto the body attachment wafers 4,4' coplanar therewith. The spaces between the coupling layers 5,5' and the body attachment wafers 4,4' schematically shown in FIGS. 1 and 2 develop due to stretching of the thin coupling layers 5, 5' by the weight of the ostomy pouches 2,2' and their content and external forces acting on the ostomy pouches. Usually the ostomy pouches are pressed against the body by the clothing of the patient and/or by other external means.

The forces from the weight of the ostomy pouch 2,2' and its content will be transferred to the body attachment wafer 4,4' mainly along the upper half of the attachment line 9,9', i.e. the weld seam connecting the outer periphery of the coupling layer 5,5' to the plastic film 6,6' of the body attachment wafer 4,4'. The forces from the weight of the ostomy pouch 2,2' and its content will thus be distributed mainly as shear forces to the upper portion of the part of the body attachment wafer lying radially outside the attachment line. The part of the body attachment wafer 4,4' lying inside the attachment line 9,9', i.e. the central part thereof, will not be influenced by said transferred forces and the risk for peel forces to appear near the inner edge of the body attachment wafer 4,4' is minimized. Thereby also the risk for liquid waste from the stoma S to leak in under the inner edge of the body attachment wafer 4,4' is minimized. In order to ensure that the outer edge of the body attachment wafer 4,4 will only be influenced by shear forces by the weight of the ostomy pouch 2,2' and its content the attachment line 9,9' of the coupling layer 5,5' should be distanced from said outer edge by at least 5 mm.

By having a coupling layer 5,5', the ostomy pouch 2,2' can be moved, for example due to movements of the wearer, without directly affecting the body attachment wafer, some movements can be taken up of the coupling layer without affecting the body attachment wafer and other movements will be transferred as shear forces in the coupling layer. By affixing the outer periphery of the coupling layer 5,5' to the body attachment wafer 4,4', the forces emanating from the ostomy pouch and acting on the body attachment wafer via the coupling layer will be distributed over a larger area of the body attachment wafer than if the ostomy pouch would be directly affixed to the body attachment wafer. The force distribution in ostomy devices according to the present invention is thus so good that the size of the body attachment wafer can be made smaller in comparison with known ostomy devices without increasing the risk for leakage or involuntary detachment of the body attachment wafer.

As is evident from FIG. 2, the inner periphery of the coupling layer 5' is affixed to the body attachment wafer 4' at a distance from the opening therein surrounding the stoma S. The opening in the body attachment wafer 4' for the stoma can, by cutting, thereby be adapted in size and shape to an individual stoma. In the embodiment according to FIG. 1, it is of course also possible to by cutting adapt the opening in the body attachment wafer 4 to the size and shape of an individual stoma The shapes of the body attachment wafers 4,4', the coupling layers 5,5' and the openings in said components are preferably circular but other shapes are possible. The shapes of the components and the openings therein can be varied, the coupling layer can for example be oval and the opening therein circular. In the figures the ostomy pouches 2,2' are shown in a vertical position but in use the ostomy pouches can be applied in other positions. However, liquid waste will always initially flow downwards in a vertical direction so the forces of the weight of the ostomy pouches and their content will influence the body attachment wafers 4,4' in the way described above independent of the positions of the ostomy pouches 2,2'.

Since the body attachment wafer in the described embodiments is very flexible it can be difficult to handle. For this reason a releasable stiffening layer in the form of a frame is releasably attached to a peripheral portion of the body attachment wafer lying outside the outer periphery of the coupling layer. This stiffening layer is removed after application of the ostomy device and is accordingly not disclosed in the figures which show the ostomy device in an applied state. The frame consists preferably of paper, thin foam or plastic film.

Furthermore, a release layer covers the adhesive layer before use of the ostomy device, which layer is removed before application of the ostomy device. The release layer consists preferably of polyethylene or a laminate of polyethylene and paper if the adhesive coating consists of silicone gel but if other skin friendly and soft adhesives are used it can consist of silicone coated paper or any other commonly used material for release layers.

The described embodiments can of course be modified without leaving the scope of invention. The attachment line extends in the described embodiments around the outer periphery of the coupling layer but can be located distanced from the outer periphery of the coupling layer, for example if the coupling layer has the same extension as the body attachment wafer, which for manufacturing reasons can be favourable, but the attachment line between the coupling layer and the body attachment wafer is distanced from the outer periphery of the body attachment wafer as is preferred. Other soft skin friendly adhesives than silicone gels can for example be used, such as soft hot melt adhesives. Furthermore, any kind of known types of ostomy pouches can be used in combination with the described coupling layer and body attachment wafer. It is also possible to use other ways than welding for the affixing of the coupling layer to the body attachment wafer, for example can adhesive be used, either a permeable adhesive or a pattern of adhesive. The scope of invention should therefore only be limited by the wording of the enclosed patent claims.

The invention claimed is:

1. An ostomy device, comprising:
   an ostomy pouch having an entrance opening,
   a body attachment wafer having a through-going opening, and
   a coupling layer having a central opening therein, wherein the coupling layer couples the pouch to the body attachment wafer,
   wherein said body attachment wafer comprises a plastic film that is coated with a layer of skin friendly adhesive on a side of the plastic film distal to the ostomy pouch, wherein the coupling layer is affixed directly to the body attachment wafer along an attachment line extending around the central opening in the coupling layer, said attachment line being distanced from the central opening in the coupling layer, and wherein the region around the entrance opening of the pouch is affixed directly to the coupling layer in a landing zone located between said attachment line and the opening in the body attachment wafer.

2. The ostomy device of claim 1, wherein the plastic film in the body attachment wafer has a thickness of 50 micrometers or less.

3. The ostomy device of claim 2, wherein the weight per unit area of the coupling layer is from 15 to 60 $g/m^2$.

4. The ostomy device of claim 3, wherein the coupling layer consists of a plastic film.

5. The ostomy device of claim 3, wherein the coupling layer consists of a polyurethane film.

6. The ostomy device of claim 3, wherein the coupling layer consists of non-permeable plastic foam.

7. The ostomy device of claim 3, wherein the coupling layer consists of a laminate of a plastic film and a nonwoven.

8. The ostomy device of claim 1, wherein the inner periphery of the coupling layer is affixed directly to the body attachment wafer, the inner periphery of the coupling layer being distanced from the outer periphery of the through-going opening in the body attachment wafer.

9. The ostomy device of claim 8, wherein the attachment line of the coupling layer is affixed directly to the body attachment wafer by a discontinuous seam.

10. The ostomy device of claim 8, wherein the coupling layer comprises perforations in an area thereof between the landing zone and the attachment line of the coupling layer.

11. The ostomy device of claim 1, wherein the skin friendly adhesive is a silicone gel adhesive.

12. The ostomy device of claim 11, wherein the silicone gel adhesive has a weight per unit area greater than 50 g/m$^2$ and a penetration value greater than 10 mm.

13. The ostomy device of claim 1, wherein the coupling layer is affixed directly to the body attachment wafer by welding.

14. The ostomy device of claim 1, wherein the attachment line of the coupling layer is distanced from the outer periphery of the body attachment wafer by at least 5 mm.

* * * * *